United States Patent [19]
Sheffield et al.

[11] Patent Number: 6,003,517
[45] Date of Patent: Dec. 21, 1999

[54] METHOD FOR USING AN ELECTROSURGICAL DEVICE ON LUNG TISSUE

[75] Inventors: Warren D. Sheffield, Loveland; Jesse Kuhns, Milford; David C. Yates, West Chester; Steven H. Mersch, Germantown, all of Ohio

[73] Assignee: Ethicon Endo-Surgery, Inc., Cincinnati, Ohio

[21] Appl. No.: 09/070,363

[22] Filed: Apr. 30, 1998

[51] Int. Cl.$^6$ .................................................. A61B 17/36
[52] U.S. Cl. ............................... 128/898; 606/41; 606/50
[58] Field of Search ............................... 128/898; 606/41, 606/42, 45–52, 142, 143; 227/175.1

[56] References Cited

U.S. PATENT DOCUMENTS

| | | |
|---|---|---|
| 5,263,629 | 11/1993 | Trumbull et al. . |
| 5,389,098 | 2/1995 | Tsuruta et al. ............................ 606/41 |
| 5,397,324 | 3/1995 | Carroll et al. . |
| 5,403,312 | 4/1995 | Yates et al. . |
| 5,503,638 | 4/1996 | Cooper et al. . |
| 5,542,594 | 8/1996 | McKean et al. . |
| 5,549,628 | 8/1996 | Cooper et al. . |
| 5,575,803 | 11/1996 | Cooper et al. . |
| 5,582,611 | 12/1996 | Tsuruta et al. . |
| 5,624,452 | 4/1997 | Yates . |
| 5,688,270 | 11/1997 | Yates et al. . |
| 5,709,680 | 1/1998 | Yates et al. . |
| 5,735,848 | 4/1998 | Yates et al. ............................... 606/48 |

OTHER PUBLICATIONS

Cooper et al, "Precision Cautery Excision of Pulmonary Lesions", The Annals of Thoracic Surgery, vol. 41, No. 1, 1986.

"Median Sternotomy for Bilateral Resection of Emphysematous Bullae", (Oriane Lima, MD et al., Journals of Thoracic Cardiovascular Surgery vol. 82, Dec. 1981).

"Aggressive Pulmonary Resection for Metastatic Osteogenic and Soft Tissue Sarcomas", (M. Wayne Flye, MD et al., The Annals of Thoracic Surgery, vol. 37 No. 2 Feb. 1984).

"Presision Cautery Excision of Pulmonary Lesions", (Joel D. Cooper, MD et al., The Annals of Thoracic Surgery, vol. 41 No. 1 Jan. 1986).

"Pulmonary Procedures Assisted by Optosurigical and Electrosurgical Devices: Comparison of Damage Potential", (Joseph LoCicero, III, MD et al,. Laser in Surgery and Medicine 1987).

"Reinforced Staple Line in Severely Emphysematous Lungs", (F.–M. Juettner, MD et al., The Journal of Thoracic and Cardiovascular Surgery vol. 97, No. 3 Mar. 1989).

"Technique to Reduce Air Leaks After Resection of Emphysematous Lung", (Joel D. Cooper, MD, Annual of Thoracic Surgery 1994).

"Unilateral Thoracoscopic Surgical Approach For Diffuse Emphysema", (Robert J. Keenan, MD et al., Journal of Thoracic and Cardiovascular Surgery, vol. 111, No. 2).

"Bilateral Pneumectomy (Volume Reduction) for Chronic Obstructive Pulmonary Disease", (J.D. Cooper, MD et al., Journal of Thoracic and Cardiovascular Surgery, vol. 109, No. 1).

"Single–Stage Bilateral, Video–Assisted Thoracoscopic Lung Volume Reduction Operation", (Wickii T. Vigneswaran, MD et al. The Annuals of Thoracic Surgery 1997).

(List continued on next page.)

*Primary Examiner*—Michael Peffley
*Attorney, Agent, or Firm*—Louis J. Capezzuto

[57] ABSTRACT

A method of resecting a portion of lung using an electrosurgical instrument is disclosed. The electrosurgical device clamps upon lung tissue and applies RF energy to create a cauterized zone within the clamped portion of the lung. At least one staple is placed within the cauterized tissue zone. The cauterized zone is cut adjacent to the at least one staple and the cut portion of the lung is removed.

12 Claims, 14 Drawing Sheets

OTHER PUBLICATIONS

"Reduction Pneumonoplasty for Emphysema", (Alex G. Little, M.D. et al., Annuals of Surgery vol. 222, No. 3,365–374).

"A Randomized, Prospective trial of Staples lung reduction versus laser Bullectomy for Diffuse Emphysema", (Robert J. McKenna, Jr., M.D. et al., The Journal of Thoracic and Cardiovascular Surgery, Feb. 1996).

"In Vitro Comparison Between Argon Beam Coagulator and Nd: YAG Laser in Lung Contraction Therapy", (Noriyoshi Sawabata, M.D. et al., Annuals Thoracic Surgery 1996; 62 1485–8).

"A New Handpiece Attachment For Nd: YAG Laser Ablation Of Emphysematous Bullae", S. Kato et al., (Nippo Kyobu Shikkan Gakkai Zasshi (Japan), May 1997, vol. 35 (5) p. 491–4.

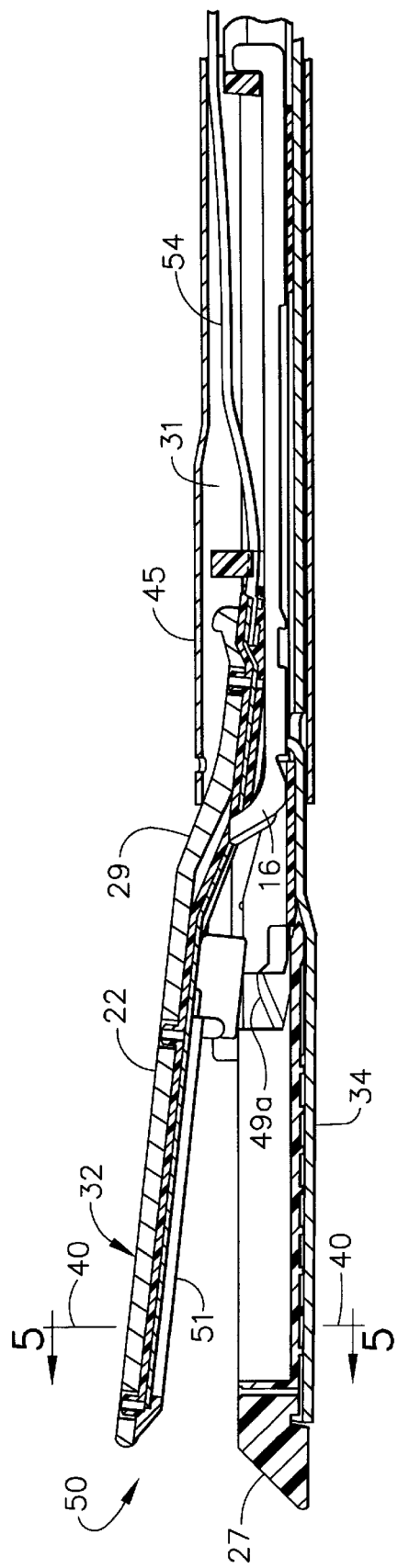
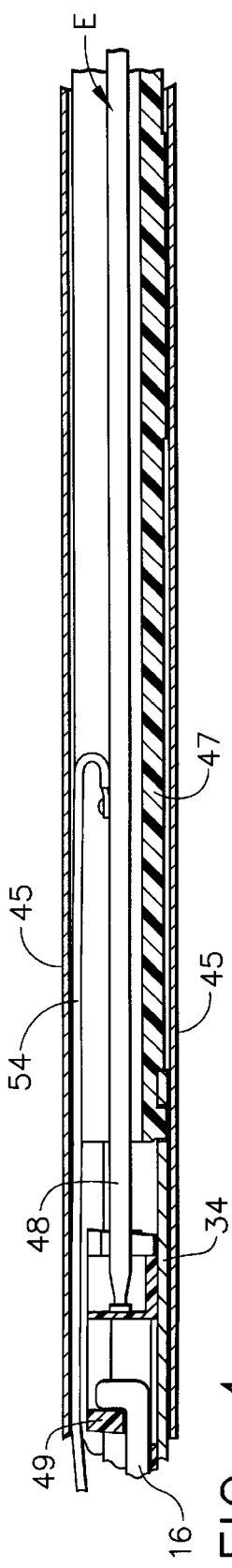

METHOD FOR USING AN ELECTROSURGICAL DEVICE ON LUNG TISSUE

FIELD OF THE INVENTION

The present invention relates, in general, to an improved method of using an electrosurgical device for cauterization, coagulation and/or tissue welding in the performance of a surgical lung volume reduction procedure.

BACKGROUND OF THE INVENTION

Lung tissue is composed of two basic types of structures, i.e. vascular networks to carry blood, and bronchial structures that carry air to oxygenate the blood. Resection of this type of tissue poses two problems to a surgeon. The first problem is achieving hemostasis of the vascular networks. The second problem is achieving pneumostasis of the bronchial structures. Additionally, since these procedures usually involve lung tissue that is frequently diseased, the diseased lung tissue is often overdistended, or inflamed, thus resulting in thin, fragile, friable tissue.

Consequently, a variety of techniques are available to surgeons as a means of controlling hemostasis and pneumostasis in lung tissue. The techniques include suturing, the application of clips, stapling, the application of RF energy, and the use of other energy modalities. A common surgical procedure is the resection of a portion of the lung as a means to remove a tumor, or as a means to reduce the lung volume in emphysemic patients.

Lung volume reduction surgery is performed on patients with emphysema wherein some of the air sacs within the lungs become overdistended or inflamed, resulting in destruction of alveolar walls. The size of the thoracic cavity is fixed, and when the diseased tissue swells, it compresses the healthy lung tissue thereby reducing the volume of air that can be ingested into the healthy portions of the lungs. This results in shortness of breath, painful breathing, and eventually could lead to right ventricular hypertrophy and heart failure.

The primary cause of emphysema is smoking, and the damaged tissue is generally confined to the upper lobes of the lungs. As a means of increasing the volumetric efficiency of the lungs, lung volume reduction surgery was developed. In this surgery, damaged portions of the lungs are removed, reducing the constricting effects caused by overdistended diseased tissue. Although the volume of the lung tissue is reduced, the elimination of diseased tissue has a dramatic beneficial effect to the patient by enabling the remaining tissue to work with increased volumetric efficiency.

Electrocautery instruments are commonly used when accessing a patient for thoracic surgery. These instruments apply monopolar or bipolar Radio Frequency (RF) energy to cauterize the "bleeders" in the chest wall as the chest cavity is being opened. Monopolar instruments have one electrode that is associated with a cutting or cauterizing instrument and a return electrode is attached to a remote portion of the patient. Hemostasis is controlled by the application of the energized device to the site of the bleeder such that the current arcs between the tip of the device and the tissue application site, thus cauterizing the bleeder.

Bipolar instruments normally apply a cauterizing current to a pair of electrodes, located within or, formed by moveable opposed jaw members of the instrument. Tissue is cauterized by placing it within the open jaw members of the instrument, closing the jaw members of the instrument upon the tissue to bring the electrodes into close proximity, and then applying RF bipolar energy to the compressed tissue within the jaw members. The current arcs between the electrodes and cauterizes, coagulates, or tissue welds the tissue compressed therein. Bipolar electrocautery has been used to resect metastic lesions in lung tissue. The procedure, using cautery forceps, was found to have a low postoperative morbidity from air leaks, but was quite lengthy. This was described in a paper by Cooper, Joel D. et al. "Precision Cautery Excision of Pulmonary Lesions", *Annals of Thoracic Surgery* 4:51–53, 1986.

Additionally, mechanical devices such as surgical staplers and linear cutters, both open and endoscopic, have also been utilized as a means of resecting diseased lung tissue. Staples have long been used to provide hemostasis in vascular structures, and when applied to lung tissue, were found to provide a good degree of pneumostasis as well. Surgical cutters have a plurality of staples held in multiple staggered rows in a replaceable cartridge. The cutters compress the lung tissue, and the staples are fired into the compressed tissue in close proximity to the diseased portion of the lung that is to be excised. A cutting blade is passed longitudinally between the innermost rows of formed staples, transecting the tissue. The cutter is removed from the surgical site, reloaded with another unfired stapling cartridge, and the procedure is repeated until the desired section of the lung is resected and removed.

One known problem which can arise with using surgical staplers in this fashion has been the formation of air leaks in the stapled lung tissue. The leaks can occur in the cut line, and/or in the staple holes themselves. Frequently, the diseased lung tissue is thin and friable and can tear at the staples as the lungs reinflate. These air leaks can be persistent and require additional surgery to locate and control. As one would expect, persistent leaks can extend the hospital stay for a patient by weeks.

As a means to alleviate the leakage problems outlined above, surgeons have developed a technique of averting the incised wall of giant bullae to act as a reinforcement for the staple line. The averted tissue provides additional material for the staples to be formed into, thereby reducing the chances of tearing at the staple line. It also reduces staple pullout in friable tissue, and results in improved pneumostasis. J. D Cooper et al. describes this procedure in a paper entitled "Median Sternotomy for Bilateral Resection Of Emphysematous Bullae", *Journal of Thoracic Cardiovascular Surgery*, Vol. 82 (1981), 892–897.

While the above technique was initially identified as a breakthrough procedure, large bullae are infrequently found within patients. This lack of available reinforcement material prompted a search by the medical community for a more easily obtainable reinforcement material. Accordingly, a variety of materials, both synthetic and natural, have been developed for use as a reinforcement material for lung resection. These materials include VICRYL® of Johnson and Johnson, New Brunswick, N.J., "DEXON®, of Sherwood-Davis and Geck, St. Louis, Mo., TEFLON®, of E. I. DuPont de Nemours & Co., Wilmington, Del., and animal material such as tanned bovine pericardium. These reinforcement materials are normally mounted into the jaw members of a linear cutter such that upon firing, the reinforcement material is stapled to the lung tissue. Optimally the, lung tissue is "sandwiched" between two layers of this reinforcement material. Use of the reinforcement material reinforces the staple line, reduces tissue tearing, and acts as a sealing material. The use of these materials, along with improved methods of attachment are disclosed in U. S. Pat.

No. 5,397,324 by Carroll et al., and U.S. Pat. Nos. 5,503,638; 5,549,628; and 5,575,803 by Cooper et al.

Although the use of an easily obtainable, easily applicable reinforcement material is a great improvement in lung surgery, there is still reluctance by the surgical community to embrace these techniques. One reason is increased surgical procedure time. Another reason is the substantial cost involved in using the reinforcement materials such as those described above. Accordingly, up until now, there is no known method of lung resection surgery that can reduce the operating time, provide improved hemostasis and pneumostasis and eliminate the need to utilize a separate reinforcement.

SUMMARY OF THE INVENTION

The present invention is a method for resecting a portion of lung comprising the following steps. First, clamping a portion of lung within an end effector of an electrosurgical instrument. Second, applying RF energy to the clamped portion of the lung to create a cauterized zone within the clamped portion of the lung. Third, stapling the cauterized zone with at least one staple. Fourth, cutting the portion of lung within the cauterized zone and adjacent to at the least one staple. After cutting, the portion of lung is removed.

The present invention provides for staples to be applied to the cauterized zone as a means of reinforcement for the cauterized zone of the lung. The present invention also provides for placing the innermost staples, e.g. a first row of staples, within the cauterized tissue zone, and outermost staples, e.g. a second row of staples outside the cauterized zone in close proximity to the cauterized tissue zone. After placing the staples, the tissue is resected within the electrosurgical device, and released upon opening of the jaw members.

In another embodiment the present invention, the staples are placed outside the cauterized tissue zone within the end effector. The stapled tissue is resected within the electrosurgical device at the cauterized zone, and the tissue is released upon opening of the jaw members.

In yet another embodiment of the present invention, the lung is clamped within the end effector of an electrosurgical instrument and staples are placed within the clamped portion of the lung. RF energy is applied to the clamped portion of the lung to create a cauterized zone adjacent to the formed staples within the clamped tissue. The cauterized zone is cut and the portion of the lung is removed.

In yet another embodiment of the present invention, the electrosurgical instrument does not have a cutting element. The end effector is clamped upon the lung tissue and bipolar energy is applied thereto. The staples are placed within the cauterized zone. The jaw members of the electrosurgical instrument are opened, and the cauterized and stapled lung tissue is removed. A separate cutting instrument is used to perform a medial transection of the cauterized tissue, between the innermost staples. Examples of a typical cutting instrument are a scalpel, a surgical scissors, or the like.

In another embodiment of the present invention, the cauterized stapled tissue is cut outside the electrosurgical device, with a cutting instrument. Staples are placed both within the cauterized tissue, and the uncauterized tissue adjacent to the cauterized tissue. The tissue is released from the electrosurgical instrument and then resected with a cutting instrument such as those identified above.

In yet another embodiment of the present invention, wherein the electrosurgical instrument does not have a cutting element, the staples are placed outside the cauterized zone. Once again, the stapled, cauterized lung is released from the electrosurgical device and resected outside of the electrosurgical instrument with a separate cutting instrument as described above.

Accordingly, the present invention, as outlined above offers several advantages over the known surgical methods of performing a lung resection procedure. The present invention offers reduced operating time, improved pneumostasis and hemostasis due to the application of bipolar RF energy and staples, and a significant reduction in cost over the known procedures that utilize a reinforcement material.

DETAILED DESCRIPTION OF THE DRAWINGS

The novel features of the invention are set forth with particularity in the appended claims. The invention itself, however, both as to organization and methods of operation, together with further objects and advantages thereof, may best be understood by reference to the following description, taken in conjunction with the accompanying drawings in which:

FIG. 3 is a cross sectional view of distal end of the instrument of FIG. 1;

FIG. 4 is a cross sectional view of the medial closure tube of the instrument of FIG. 1;

Figure 1:
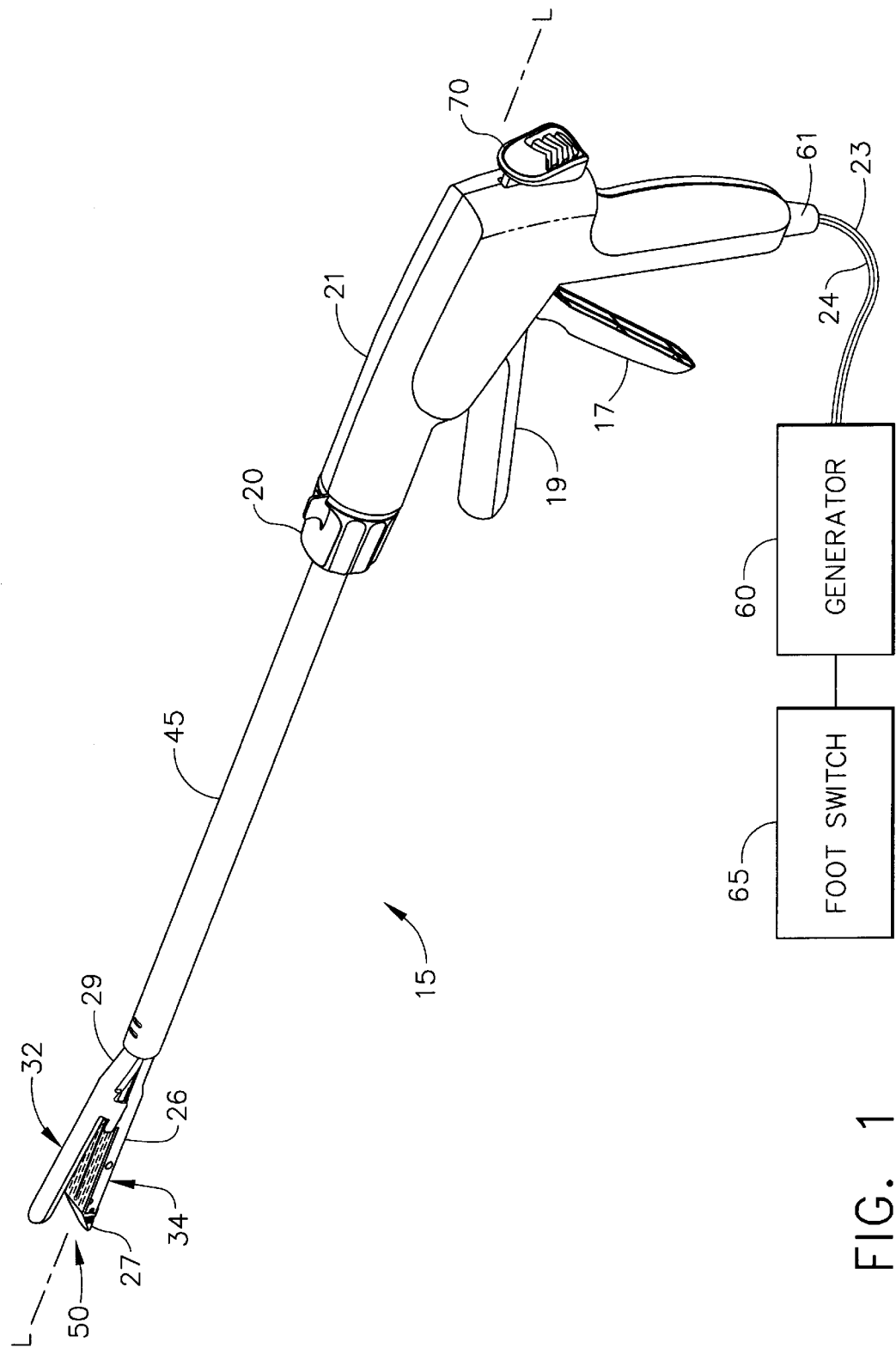
FIG. 1 is a perspective view of a electrosurgical linear stapling and cutting instrument of the present invention.
Figure 14:
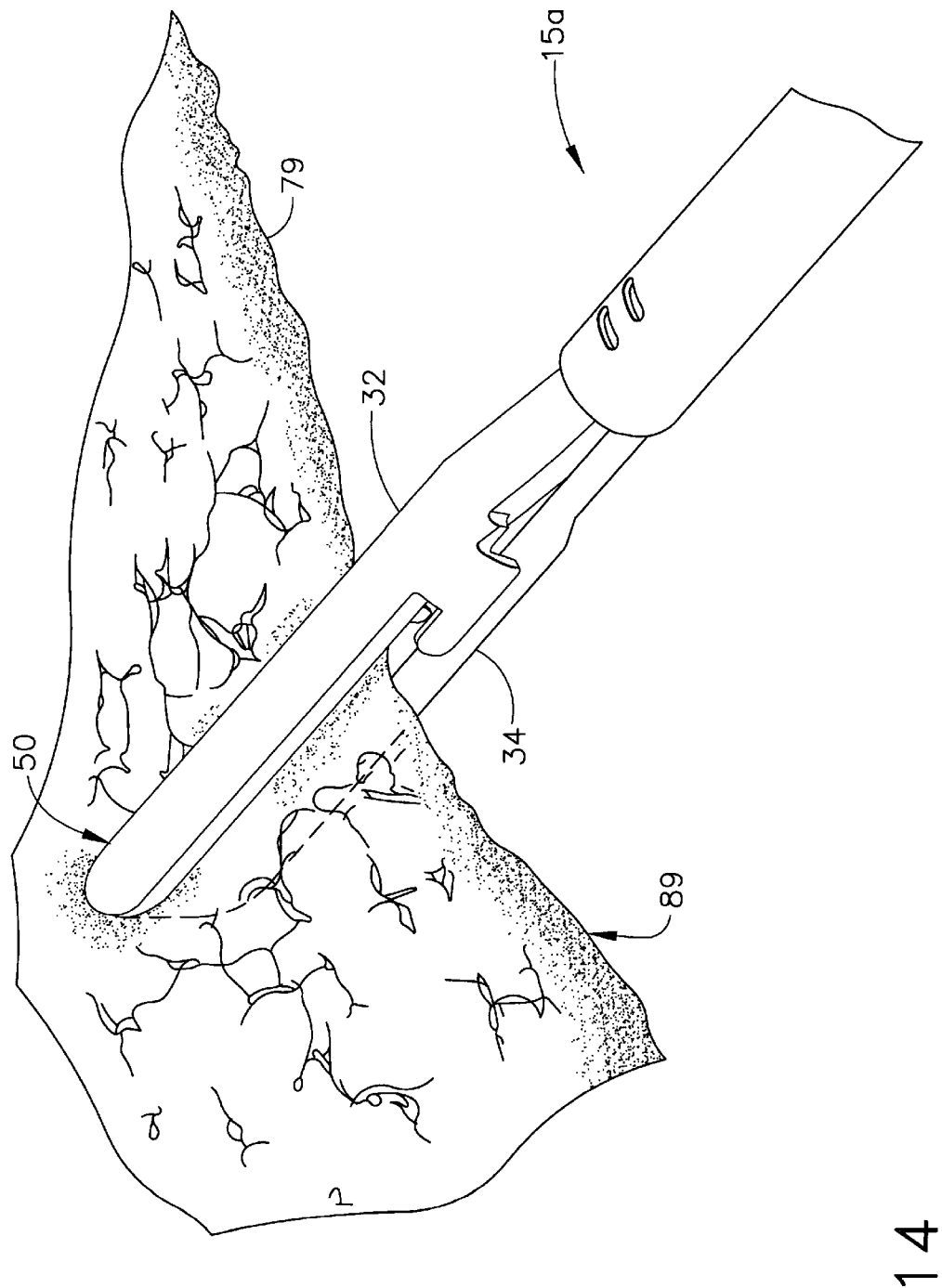
Figure 15:
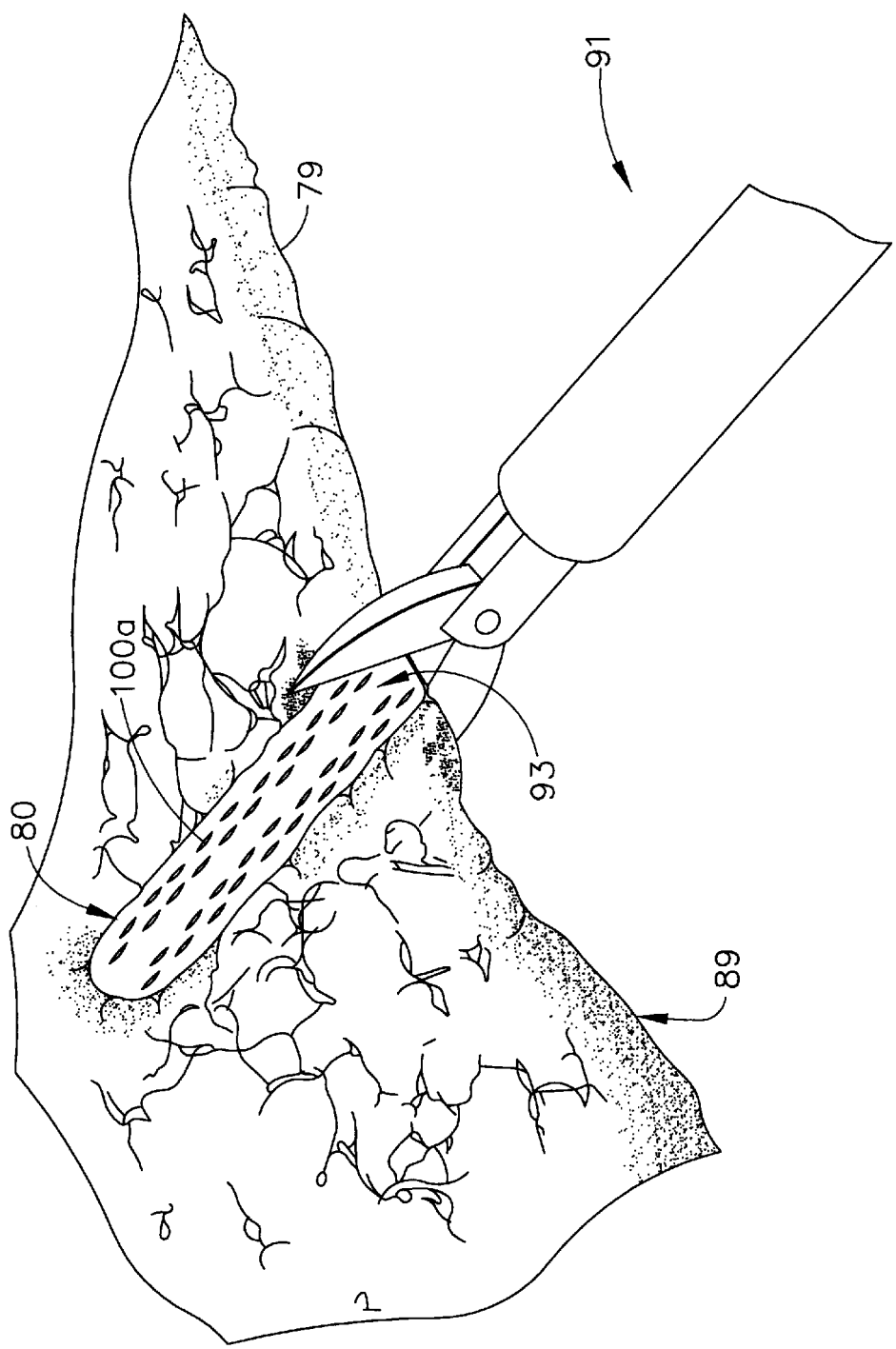

FIG. 14 is a perspective view of the of the distal end of the instrument of FIG. 1, without a cutting element, wherein the distal end of the instrument is closed, thereby compressing the portion of lung within the jaw members, RF energy is applied to the compressed tissue to create a cauterized zone and staples are placed within the cauterized zone; and FIG. 15 is a perspective view wherein the compressed tissue of FIG. 14 has been cauterized, staples have been applied to the cauterized zone, the electrosurgical device has been removed, and the cauterized zone is been transected by a surgical scissors.

DETAILED DESCRIPTION OF THE INVENTION

As best shown in FIG. 1, the present invention includes an electrosurgical instrument, generally designated 15, used for the cauterization, coagulation and/or tissue welding in the performance of surgical lung procedures. The instrument 15 is generally used for either endoscopic or open lung procedures, and is generally of the type of electrosurgical instruments described in the U.S. patent application Ser. No. 08/856,210 filed May 14, 1997; U.S. Pat. Nos. 5,403,312 and 5,688,270 which are incorporated herein by reference.

The electrosurgical instrument 15 provides pneumostasis and hemostasis when resecting lung tissue. The instrument 15 has a body 21 at a proximal end of the instrument 15 and an elongated closure tube 45 connected to the body 21. The instrument 15 also includes distal end effector 50 adjacent the distal end of the closure tube 45. A rotation knob 20 is located between the body 21 and closure tube 45 for simultaneous rotation of the closure tube 45 and the end effector 50. The end effector 50 has an upper jaw member 32 and a fixed lower jaw member 34. The upper jaw member 32 is moveable from a first open position to a second clamped or closed position. A cartridge 27 which contains a plurality of staples 100 (FIG. 5) is removably mounted within the lower jaw member 34. A clamping trigger 17 and a firing trigger 19 are rotatably mounted within the body 21. Actuation of the clamping trigger 17 results in closure of the upper jaw member 32. A release button 70 is located at the proximal end of the body 21 for unlocking the upper jaw 32 from its clamped position.

The instrument 15 is connected to an electrosurgical generator 60 that is user actuated by a footswitch 65. A first pole wire 23 and a second pole wire 24 connect the generator 60 to the instrument 15 for delivery of RF energy to the instrument 15. The first and second pole wires 23 and 24 respectively extend within from a strain relief 61 through the body 21.

Figure 2:
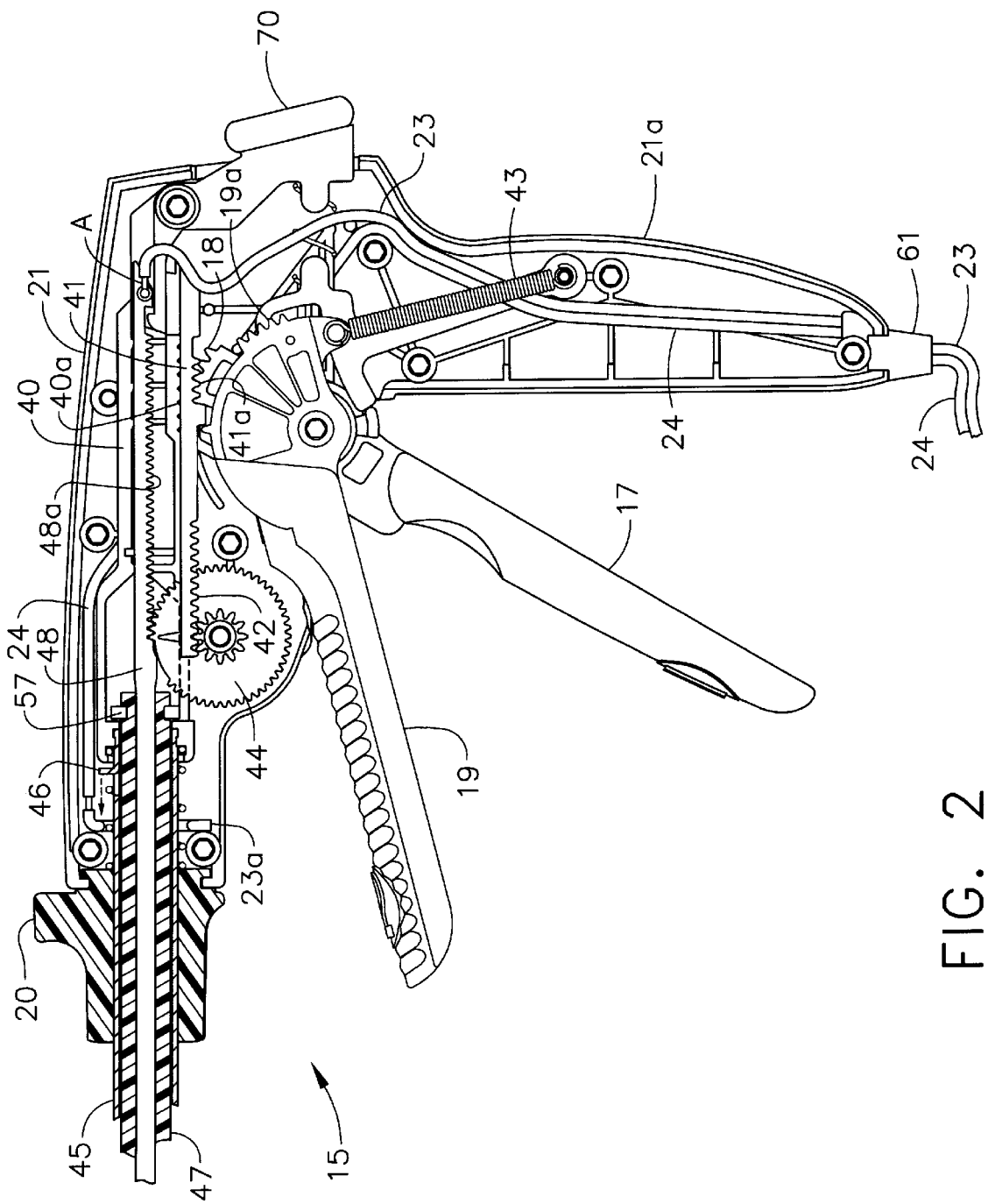
FIG. 2 is a cross sectional view of the proximal body of the instrument of FIG. 1.

The elongated closure tube 45 has a lumen 31 and a retainer 47, made of a nonconductive material, extending therein (see FIGS. 2–4). The proximal end of the retainer 47 extends from the proximal end of the closure tube 45. The lower jaw member 34 of the end effector 50 is fixedly mounted to the distal end of the retainer 47 and extends from the distal end of the closure tube 45. The closure tube 45 is moveable proximally and distally relative to the lower jaw member 34 and the retainer 47. The closure tube 45, retainer 47, and end effector 50 are constrained to rotate together about the longitudinal axis with the rotation of the rotation knob 20.

As best shown in FIG. 2, the clamping trigger 17 has a clamping trigger gear segment 18 rotatably mounted within the body 21. Actuation of the clamping trigger 17 engages the clamping trigger gear segment 18 with a yoke gear rack 40a, located on a yoke 40. Thus, actuation of the clamping trigger 17 moves the yoke 40 distally within the body 21.

The proximal end of the closure tube 45 is fixedly and rotatably coupled to the distal end of yoke 40. This coupling fixes the closure tube 45 to move longitudinally with the yoke 40, yet allows rotation of the closure tube within the yoke 40. The proximal end of the retainer 47 attaches in a similar fashion to a fixed fork 57 extending from the body 21. Distal movement of the yoke 40 causes the distal end of the closure tube 45 to engage with a camming surface 29 located on the upper jaw member 32, thus closing the upper jaw member 32. Full actuation of the clamping trigger 17 results in the upper jaw member being fully closed and engagement of the yoke 40 with the release button 70. This actuation locks the clamping trigger 17 in a closed position, and rotates the firing trigger 19 into an actuation position, e.g. the position or location formerly occupied by clamping trigger 17.

The firing trigger 19 has a firing trigger gear rack segment 19a. A short rack 41 has a short rack gear rack 41a and a pinion gear rack 42. The short rack 41 is longitudinally moveable within the body 21. Actuation of the firing trigger 19 rotates the firing trigger gear segment 19a into engagement with the short rack gear rack 41a thus driving the short rack 41 distally within the body 21. The pinion gear rack 42 of the short rack 41 engages a pinion 44 and rotates the gear counterclockwise as the firing trigger 19 is actuated. A firing rod 48 has a firing rack 48a such that counterclockwise rotation of the pinion 44 engages the outer gear teeth of the pinion 44 with the firing rack 48a resulting in distal movement of the firing rod 48 within the instrument 15.

The second pole wire 24 is terminated by a contact ring 24a that is fixedly mounted to the body 21 adjacent to the distal end of the body 21. A closure tube contact arm 46 is bent outwardly from the closure tube 45. The closure tube 45 and contact arm 46 are formed from a conducting material such as, but not limited to, steel, stainless steel, or aluminum to conduct RF energy therethrough. Actuating the clamping trigger 17 moves the closure tube 45 distally and brings the contact arm 46 into contact with the electrically conductive contact ring 23a to electrically connect the closure tube 45 with the second pole wire 24. The distal end of the closure tube 45 contacts the camming surface 29 of the upper jaw member 32 for conduction of second pole RF energy to the upper jaw member 32.

Referring now to FIGS. 3 and 4 showing the cross section of the end effector 50 and the closure tube 45, the distal motion of the firing rod 48 engages a pusher block 49 with the distal end of the firing rod 48. The pusher block 49 is slideably moveable longitudinally within the closure tube 45 and connects the firing rod 48 to a cutting element 16, and a plurality of firing wedges 49a. Distal or proximal movement of the firing rod 48 results in like movement of the firing wedges 49a and the cutting element 16. The distal motion of the firing rod 48 moves the firing wedges 49a into the cartridge 27. The first pole wire 23, located within body 21, is fixedly connected to the proximal end of the electrically conducting firing rod 48 to conduct RF energy thereto. The firing rod 48 is constructed from a conducting material such as steel, stainless steel, aluminum or any material having a conductive coating. As best shown in FIG. 4, an electrode wire 54 is conductively attached to the firing rod 48 near to the distal end of the firing rod 48. The electrode wire 54 extends distally to the end effector 50 for conduction of first pole RF energy thereto. The distal end of electrode wire 54 is conductively attached to anvil 22.

Figure 5:
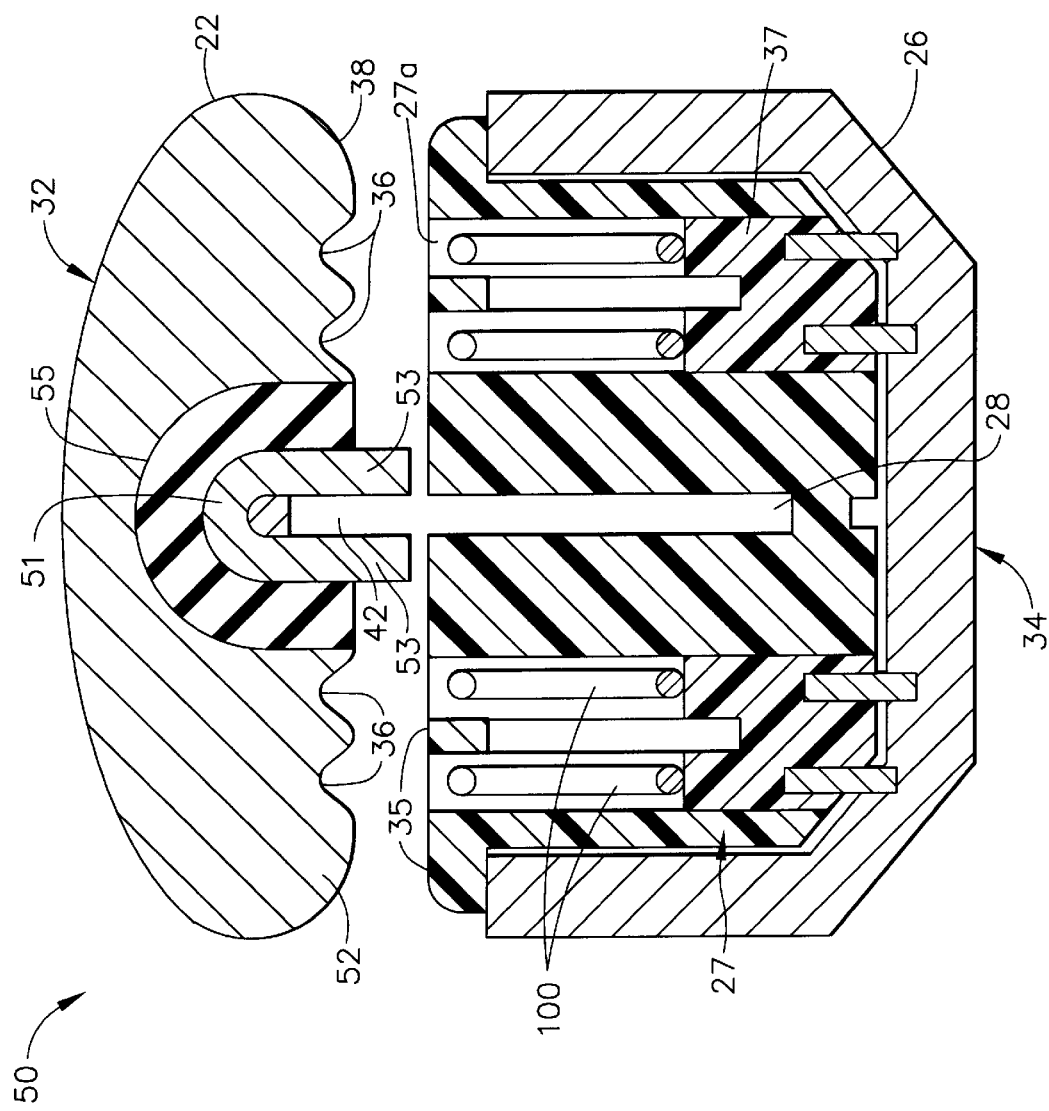
FIG. 5 is a front cross sectional view of the distal end of the instrument of FIG. 3 taken along the line 5—5.

As best shown in FIG. 5, the upper jaw member 32 has a conductive "U" shaped first pole electrode 51, a "U" shaped insulator 55 adjacent to the first pole electrode 51, and a conductive anvil 22 acting as a second pole electrode 52. The first pole electrode 51 is electrically isolated from the second pole electrode 52 within the upper jaw member 32 by insulator 55 located therebetween. The first pole 51 has electrode bars 53 to contact tissue. Anvil 22 also includes an upper jaw surface 38 which is a ridged surface.

The first pole wire 23 is normally electrically connected to the first pole electrode 51 at all times. The second pole wire 24 is electrically connected to the second pole electrode 52, eg. conductive anvil 22, when the clamping system is actuated. The distal end of the closure tube 45 contacts the camming surface 29 of the upper jaw member 32 for conduction of second pole RF energy to the upper jaw member 32.

As shown in FIG. 5 the cartridge 27 has a plurality of cartridge pockets 27a. Each pocket 27a contains a staple driver 37 and a staple 100. The cartridge 27 has a knife channel 28 extending longitudinally within the cartridge 27 for passage of the cutting element 16, and the plurality of unformed "U" shaped staples 100 are arranged within parallel longitudinal rows. The upper jaw member 32 includes an anvil 22 and an upper jaw surface 38. A plurality of staple pockets 36 are formed in the upper jaw surface 38 and align with the cartridge pockets 27a. The anvil 22 is made of conductive material. The firing wedges 49a engage the staple drivers 37 and push the unformed staples 100 from the cartridge 27 through cartridge pockets 27a to the anvil 22 of the upper jaw member 32 to make formed staples 100a (see FIGS. 9–12). Upon firing, the cutting element 16 advances through the cartridge 27 proximally to the firing wedges 49a.

The electrosurgical instrument 15 has three systems; a clamping system to compress tissue within the jaw members 32 and 34 of the end effector 50, a RF electrocautery energy delivery system to cauterize tissue located therein, and a firing system that places the plurality of staples 100 (FIGS. 8–10) within the tissue and cuts the tissue between the innermost rows of staples with the cutting element 16 which is moveably advancable within the end effector 50 to resect the cauterized tissue after the staples 100a have been placed.

The clamping system includes the clamping trigger 17 pivotably mounted within the body 21. Actuation of the trigger 17 results in the closing of the upper jaw member 32 onto the lower jaw member 34. The jaw members 32 and 34 of the clamping system of the instrument 15 are sufficiently stiff to provide pressure, when closed, in a range which facilitates the cauterization of lung tissue compressed within the jaw members, and the formation of staples 100a within the compressed tissue. Full actuation of the clamping trigger 17 closes the upper jaw member 32 onto the lower jaw member 34, engages the clamping trigger 17 with the release button 70, rotates the firing trigger 19 into the actuation position 19, and electrically connects the second pole wire 24 to the second pole electrode 52 as described above. Thus, the clamping system must be actuated to electrically connect the energy delivery system, within the end effector 50 to the electrosurgical generator 60.

The energy delivery system of the present invention delivers bipolar energy from the electrosurgical generator 60. The electrosurgical generator 60 is controlled by the user by a footswitch 65. Bipolar energy is delivered to the end effector 50 when both the clamping system and footswitch 65 are actuated.

When the footswitch 65 is actuated, bipolar energy is conducted from the generator 60, through the insulated wires 23 and 24 and into the end effector 50. As best shown in FIG. 5, the electrodes of the electrosurgical instrument are located within the upper jaw member 32. Closing the upper jaw member 32 upon lung tissue 79 (FIG. 7) clamps the lung tissue 79 between an inner surface 35 of the cartridge 27, the ridged upper jaw surface 38 of the anvil 22, and the electrode bars 53. As bipolar energy is applied to the first pole 51, the current flows from the electrode bars 53, through the tissue 79, to the second pole electrode 52 and creates a cauterized zone 80 within the end effector 50.

The firing system is actuated after the tissue is cauterized by the energy delivery system. The end effector 50 has the staple cartridge 27 removably mounted within the cartridge channel 26 of the lower jaw member 34. After the end effector 50 is clamped on cauterized lung tissue, actuation of the firing trigger 19, drives the unformed staples 100 from the cartridge 27 into the cauterized zone 80 to become formed staples 100a. The cutting element 16 lags the staple formation and advances medially between the innermost rows of staples 100, hereby resecting the tissue. Once fired, the instrument 15 can be reloaded by deactivating the closure system by pressing release button 70, removing the instrument 15 from the surgical site, and replacing the cartridge 27.

METHOD ACCORDING TO THE PRESENT INVENTION

Figure 6:
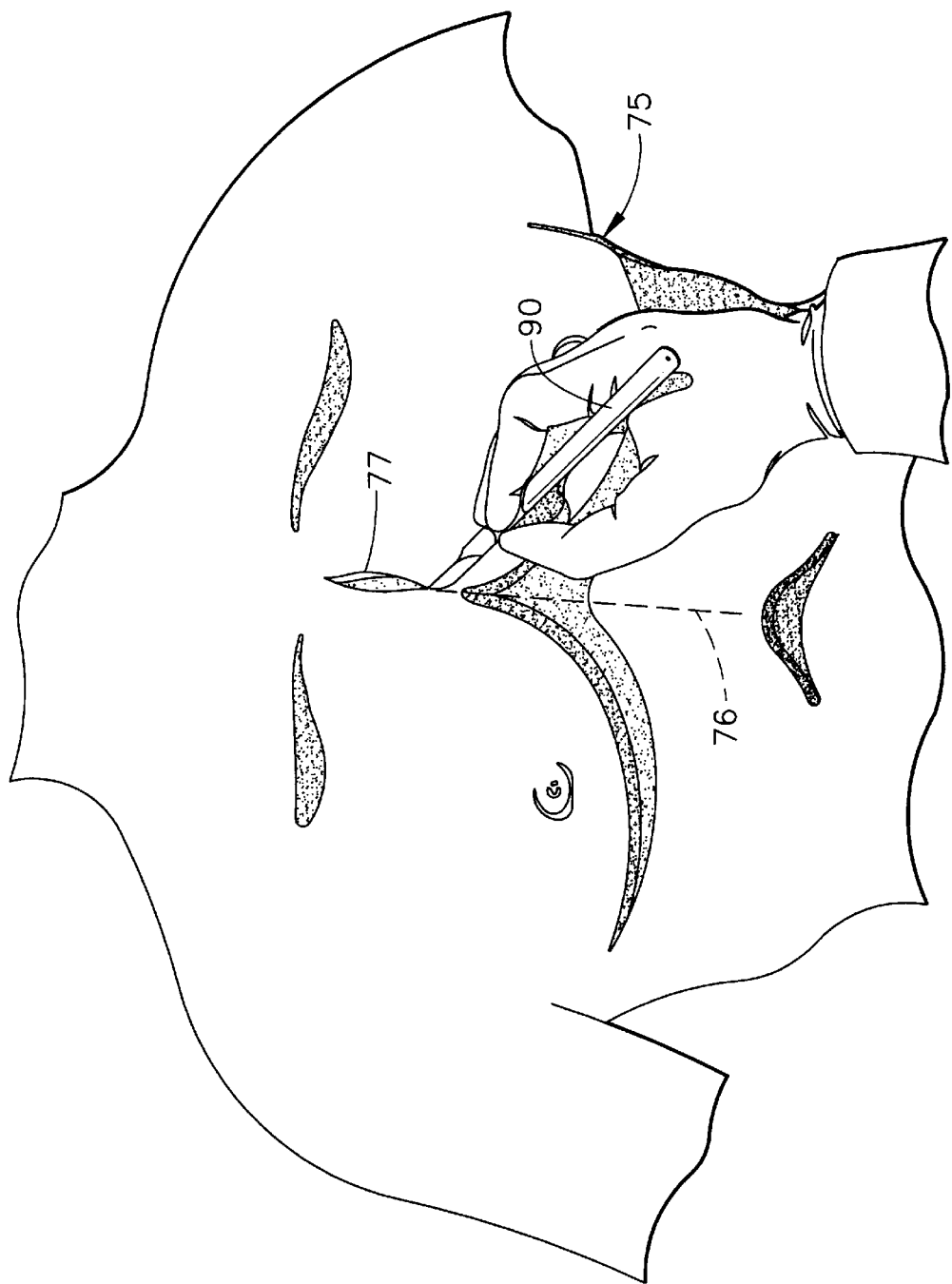
FIG. 6 is a perspective view of the surgeon performing a median incision as the first step in performing a median sternotomy on a patient.

Referring to FIG. 6, an incision location is marked on a patient's chest 75 as a drawn midline 76 beginning several centimeters (cm) below to the jugular notch and extending to within several cm. below the xiphoid. An incision 77 is made along the drawn midline 76. The incision 77 is deepened through the subcutaneous tissue to the sternum. If small bleeders are present in the incision 77, the surgeon may use any one of a number of known techniques to coagulate them. After making the initial incision 77, it is extended to the anterior table of the sternum. The superior angle of the skin flap is lifted to expose the upper border of the nubrium, thus visualizing the jugular notch. The xiphod is freed and the space behind the xiphoid and sternum is freed by passing a finger behind the sternum into the anterior mediastinum. Additionally, a finger is used to bluntly dissect behind the upper sternum. The sternum is scored along the midline 76 with a cutting instrument 90 such a scalpel or a monopolar cautery device.

Figure 7:
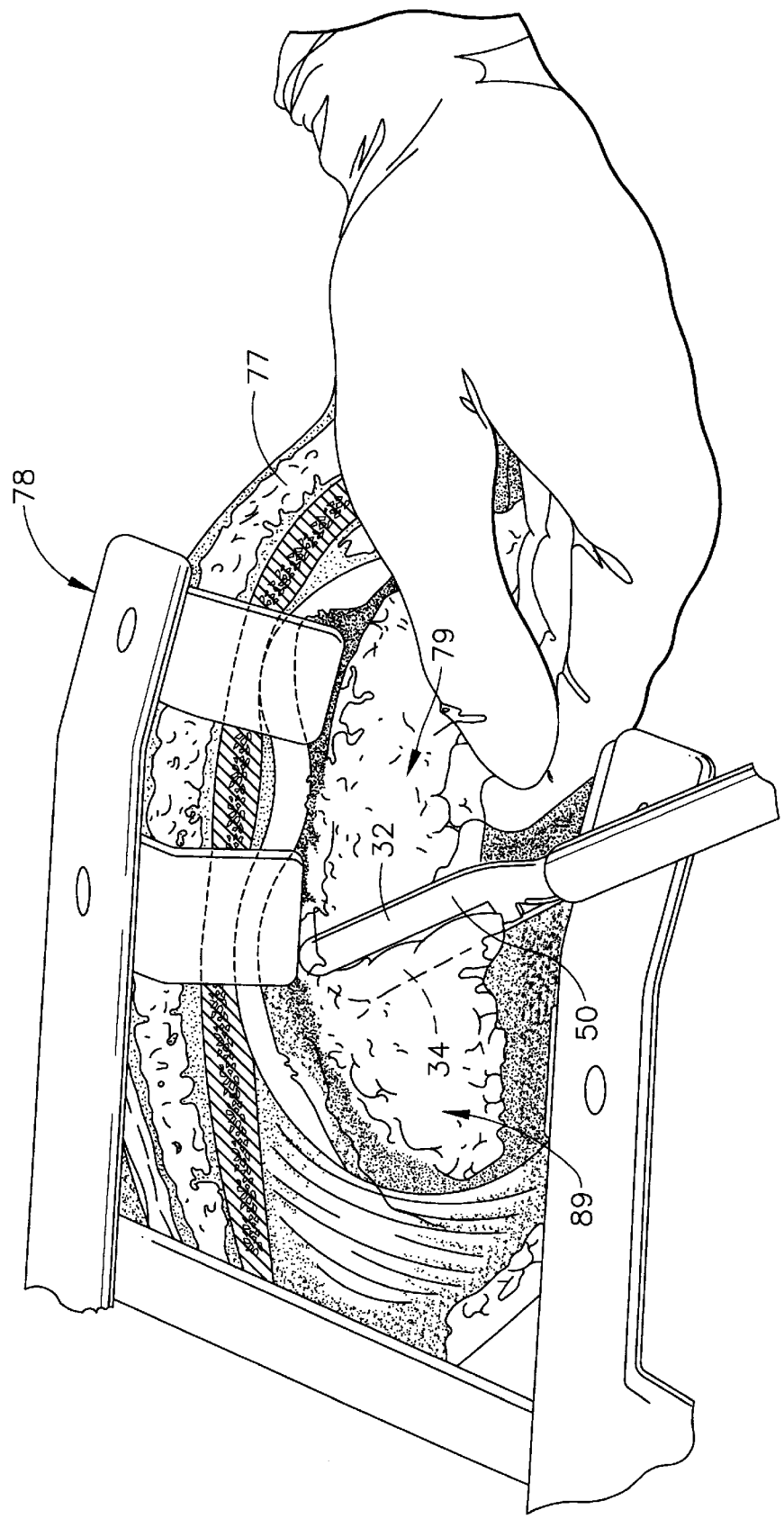
FIG. 7 is a perspective view of the completed median sternotomy of FIG. 6 wherein the surgeon is lifting a portion of the left lung within the thoracic cavity and is positioning the open distal end of the instrument of FIG. 1 over the upper lobe of the left lung.

Lungs 79 are temporarily deflated and the sternum is divided by a sternal saw or similar instrument resulting in access to the lungs 79 as shown in FIG. 7. The cut edges of the sternal incision 77 are sealed by monopolar electrocautery to reduce bleeding from the marrow located therein. Additional bleeders on the anterior and posterior sides of the sternum are cauterized. After hemostasis is obtained, a sternal retractor 78 is carefully placed in the mid portion of the sternum and opened a few turns at a time to avoid sternal fractures. The sternal retractor 78 is opened until the thoracic cavity is exposed.

Figure 8:
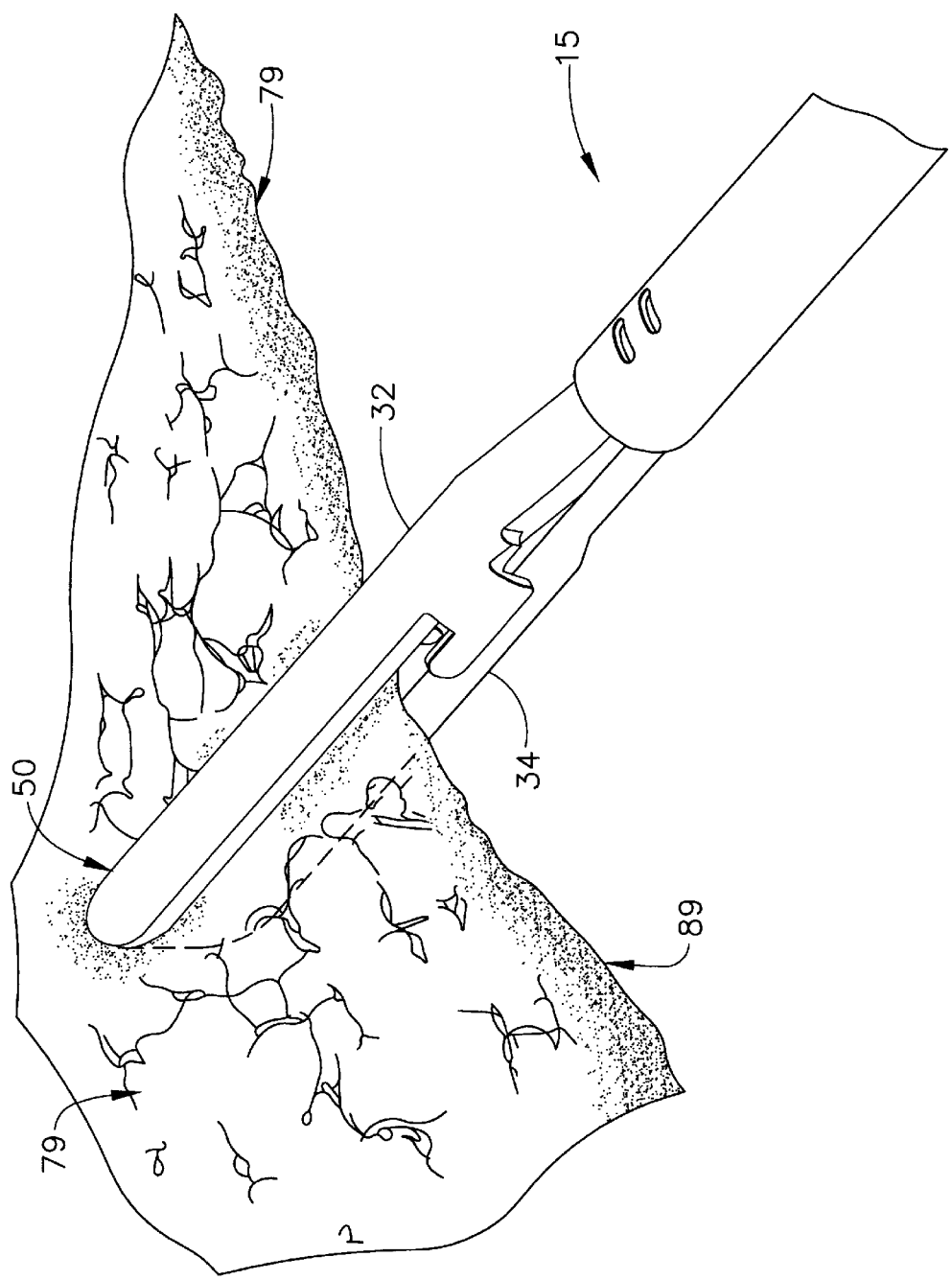
FIG. 8 is a perspective view of the of the distal end of the instrument of FIG. 1 wherein the distal end of the instrument is clamped, thereby compressing the portion of lung within the jaw members, RF energy is applied to the compressed tissue to create a cauterized zone, staples are placed within the cauterized zone, and the cauterized tissue is resected.
Figure 9:
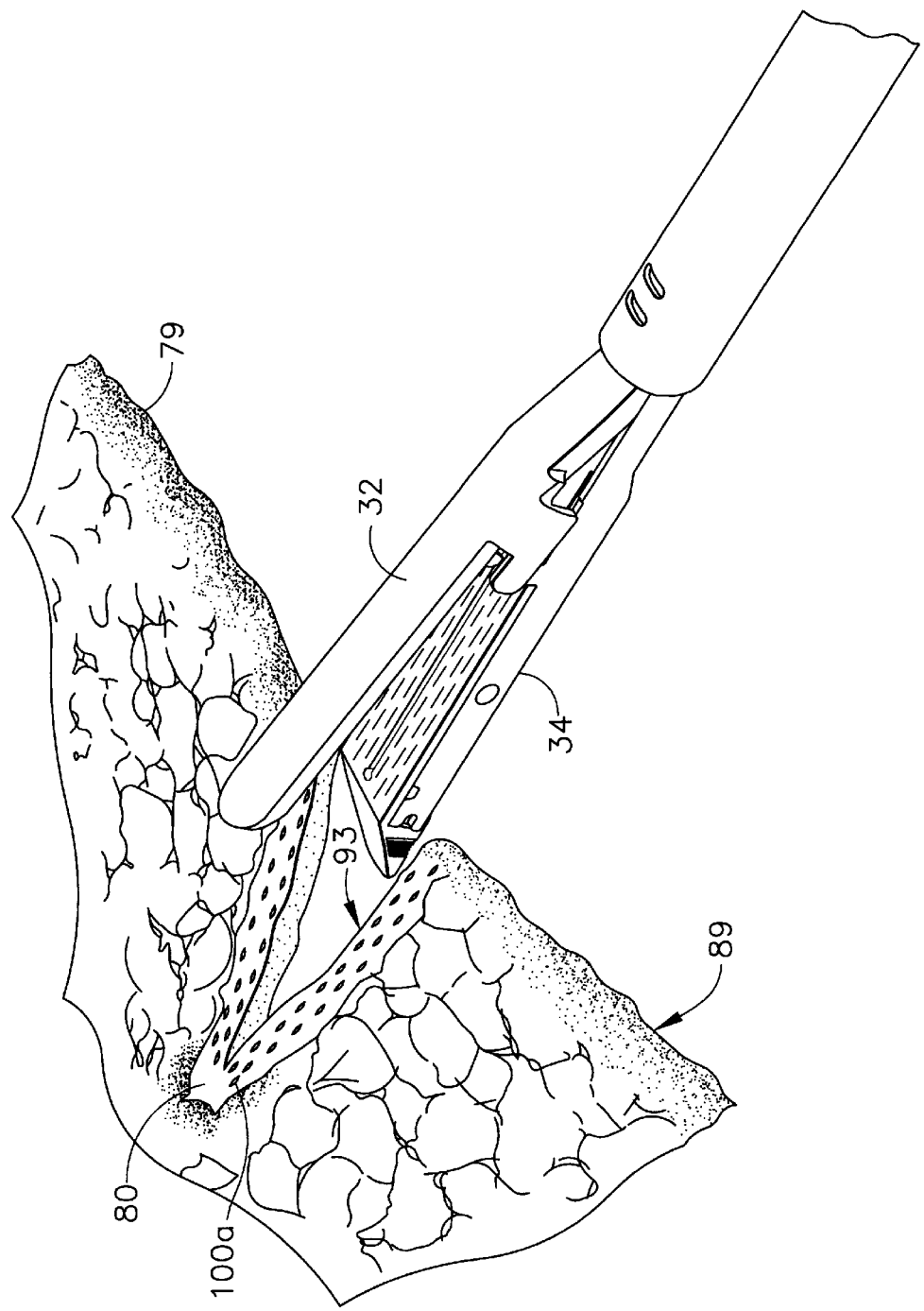
FIG. 9 is a perspective view of the of the open distal end of the instrument of FIG. 1 wherein the compressed tissue of FIG. 8 has been cauterized, staples have been applied to the cauterized zone, and the cauterized zone has been transected.

Upper lobes 89 of the lungs 79 are examined and the apicoposterior segments of the right and left upper lobes 89 are identified for transection. The jaw members 32 and 34 of the electrosurgical instrument 15 are opened and loaded with the staple cartridge 27 containing the plurality of staples 100 in two or more rows (FIG. 5). A power cord is connected to the bipolar RF generator 60. The jaw members 32 and 34 of the end effector 50 are placed over the upper lobe 89 of the left lung 79 in the desired area and are closed by actuating the clamping trigger 17 of the instrument 15 as shown in FIGS. 7 and 8. The surgeon then applies bipolar RF energy to the electrosurgical instrument 15 by depressing the foot switch 65 of the generator 60 (FIG. 1) until the cauterization is complete. Complete cauterization of the lung tissue 79 may be signaled by an alarm if one is utilized. The application of RF energy to the tissue 79 results in a cauterized zone 80 in the upper lobe 89 as shown in FIG. 9. Once the cauterized zone 80 is formed, the firing trigger 19 of the electrosurgical instrument 15 is actuated to place the rows of staples 100a into the cauterized zone 80. Once the staples 100 are formed upon firing, the cutting element 16 (FIG. 2) is advanced in order to cut within the cauterized zone 80 between the innermost rows of formed staples 100a. The jaw members 32 and 34 of the instrument 15 are opened and removed from the lung tissue 79.

Figure 13:
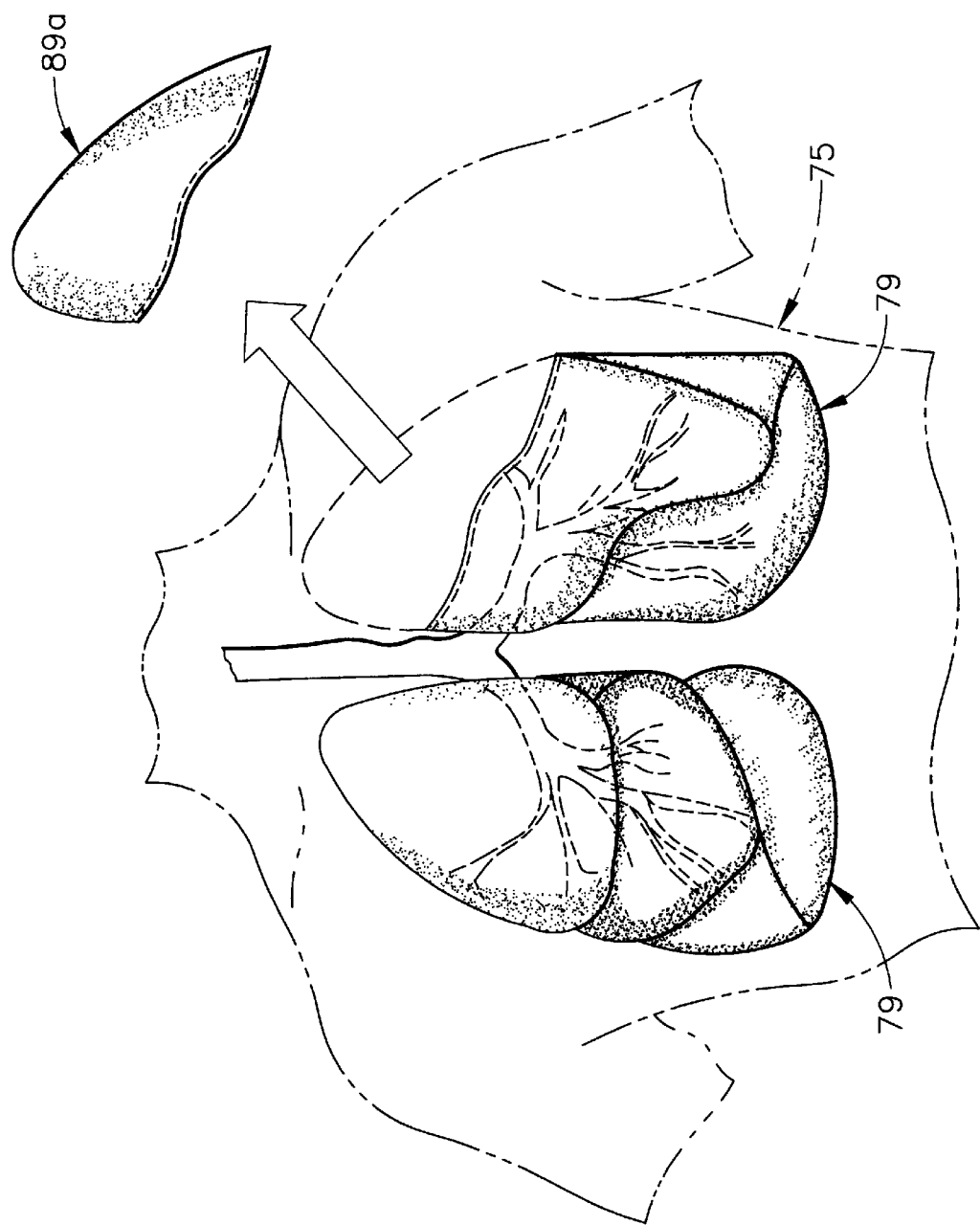
FIG. 13 is a front view of a patients lungs superimposed on an outline of the patient showing the removal of the upper left lobe of the lung after performing a lung volume reduction surgery, according to the present invention.

Once the jaw members 32 and 34 of the electrosurgical instrument 15 are opened, the instrument 15 is removed from the surgical site. The empty cartridge 27 is removed, and a new cartridge 27 is reloaded. Upon reloading, the instrument 15 is returned to the surgical site and the instrument 15 is reapplied or placed on the lung 79. This process is repeated until the desired portion of the upper left lobe 89 is transected. A transected upper left lobe 89a is removed from the patients chest 75 as best shown in FIG. 13. If required, these steps will also be applied to other portions of the lung 79.

Figure 10:
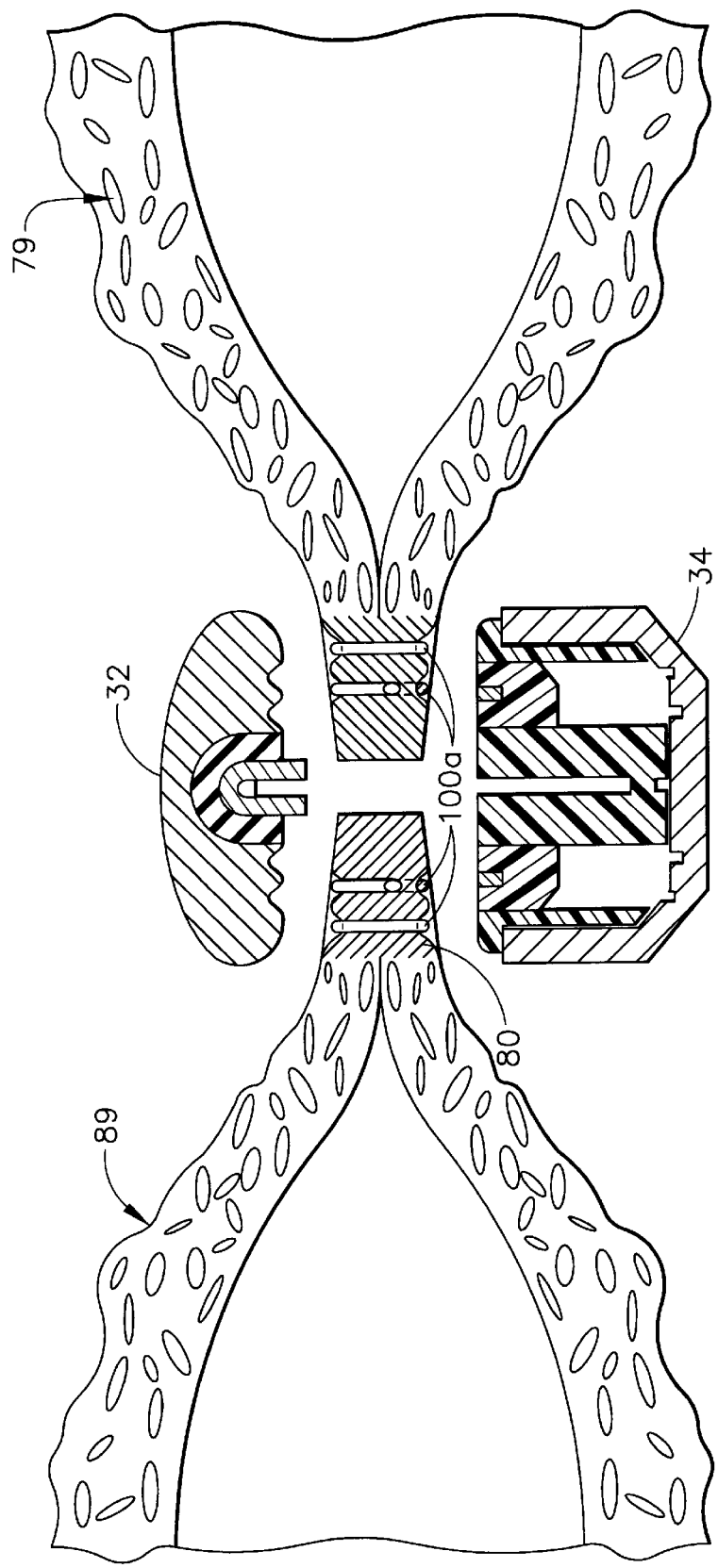
FIG. 10 is a front cross sectional view of the distal end of the instrument of FIG. 3 and the cauterized, stapled, and transected lung tissue of FIG. 7, wherein all rows of staples are placed within cauterized tissue.

The method according to the present invention utilizing the electrosurgical instrument 15 is paramount to the effectiveness of the lung resection. Since the lung tissue 79 is formed from vascular networks, bronchial networks, and alveoli air sacs, it becomes critical that the tissue 79 be initially compressed to bring the myriad passageways and air sacs together into a compressed mass prior to the application of bipolar energy. Once the tissue is compressed, the introduction of bipolar energy to the tissue 79 cauterizes, coagulates, or tissue welds the compressed tissue 79 together to form cauterized zone 80 that acts as a hemostatic and pneumostatic seal. As a means of reinforcement, multiple rows of formed staples 100a are placed within the cauterized zone 80. A cross section view of the results of this method is shown in FIG. 10.

Figure 11:
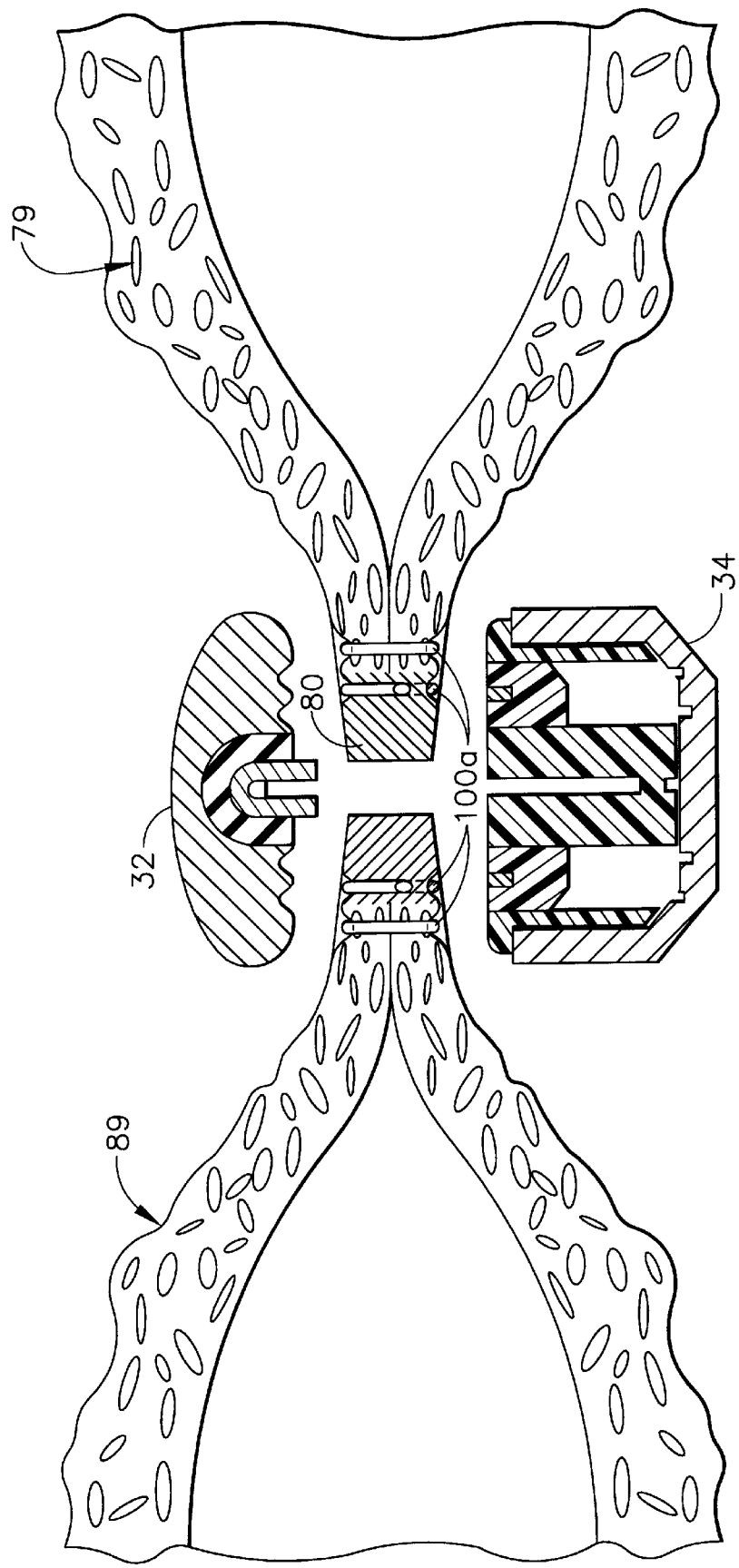
FIG. 11 is a front cross sectional view of the distal end of the instrument of FIG. 3 and the cauterized, stapled, and transected lung tissue of FIG. 7, wherein the outermost rows of staples are placed within uncauterized tissue, and the innermost rows are placed within cauterized tissue.

In another embodiment of the present invention, the multiple rows of reinforcing staples 100a are placed within the cauterized zone 80 and outside the cauterized zone 80. As best shown in FIG. 11, the innermost rows of formed staples 100a are applied within the cauterized zone 80, and the outermost rows of formed staples 100a are placed outside of the cauterized zone 80 within close proximity to it within the end effector 50. The cauterized tissue 80 is then transected with the instrument 15 and the instrument 15 is opened and the transected lobe 89 of lung 79 is removed.

Figure 12:
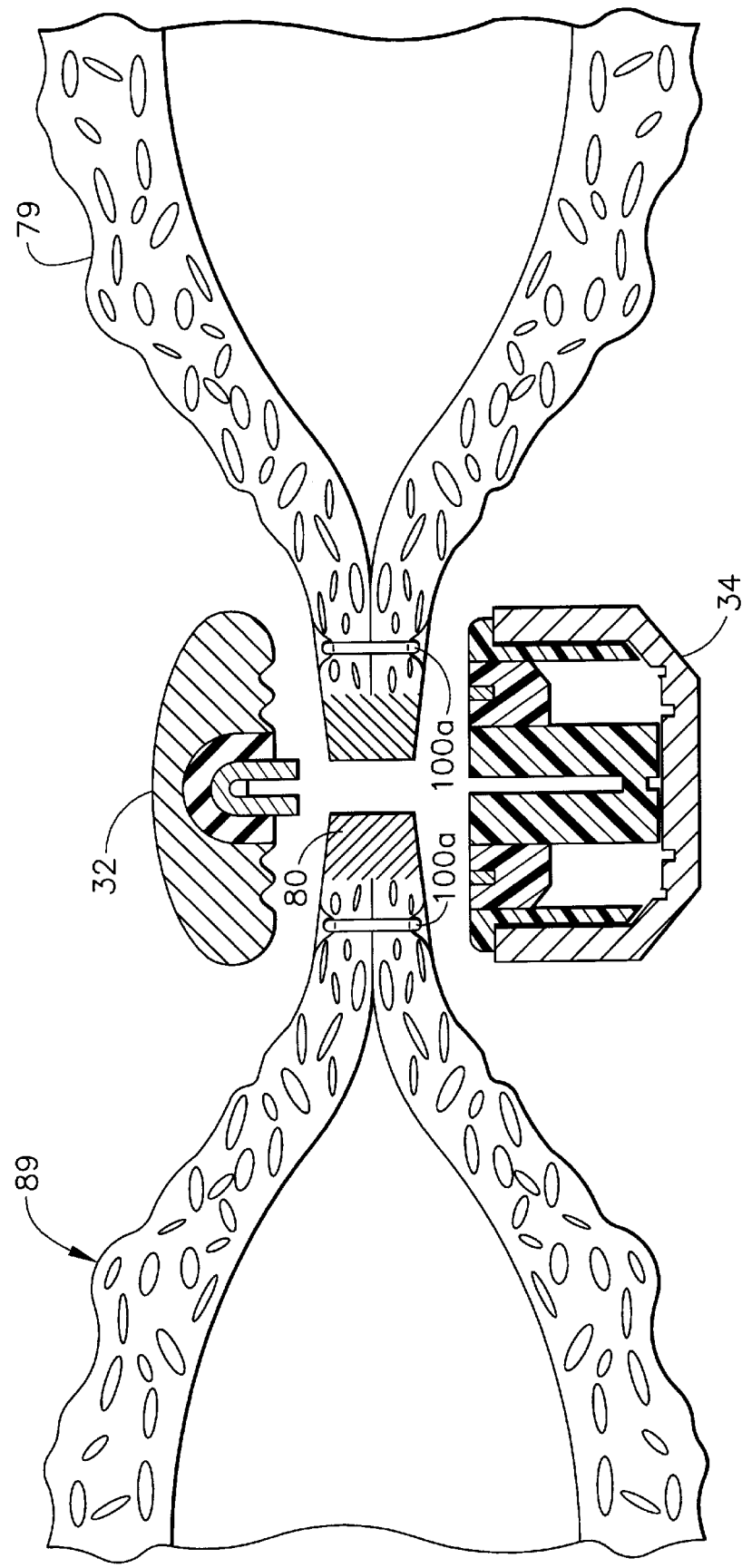
FIG. 12 is a front cross sectional view of the distal end of the instrument of FIG. 3 and the cauterized, stapled, and transected lung tissue of FIG. 7, wherein the staples are placed within the uncauterized tissue, lateral to the cauterized tissue, and the cut line is placed through the cauterized tissue.

In yet another embodiment of the present invention, as best shown in FIG. 12, the staples 100a are placed within uncauterized tissue 79 outside of the cauterized zone 80, but within close proximity to the cauterized zone 80.

Additionally, the present invention is not limited to solely a method where energy is applied to the tissue 79 prior to the placement of the staples 100a. It is well within the scope of the present invention to employ the method of use such that the staples 100a are placed prior to the application of bipolar energy. Thus, the staples 100a can be placed within the tissue clamped within the end effector 50, prior to the application of bipolar energy. This can occur when the lateral distance from the staples to the first pole electrode 51 is large enough to ensure that the bipolar energy does not approach the placed staples 100a. Preferably, the lateral distance ranges from 0.025 inches to 2.00 inches from the median cut line 93 of the cauterized zone 80.

Whereas the preferred embodiment of the electrosurgical device 15 has a cutting element 16 that transects the cauterized tissue 80 upon actuation of the firing trigger 19, an equivalent resection, as shown in FIGS. 14 and 15, can be made with two instruments, an electrosurgical instrument 15a, without a cutting element, that can compress, cauterize, and staple the tissue, and a separate cutting instrument 91 to transect the tissue once it is removed from the electrosurgical instrument. Examples of an appropriate cutting instrument 91 are a scalpel or a surgical scissors.

Accordingly, since the present invention utilizes energy and staples, this method provides improved pneumostasis and hemostasis when applied to lung tissue 79. Moreover the present invention provides the surgeon with superior method lung resection over the known methods, i.e. at a reduced cost and in a reduce period of time.

Additionally, resections are used on lung tissue 79 for other reasons than a lung volume reduction procedure. The method according to the present invention can also be utilized for the removal of a tumor by a lung resection. If a human patient is diagnosed with a benign mediastinal tumor (not shown) located on any portion of the left lung 79, a thoracoscopic lung wedge resection can be performed to excise the tumor. Instead of firing the instrument 15 straight across the lung 79 such as shown in FIG. 13, the instrument 15 is positioned near to the tumor at approximately a ninety degree orientation to the initial staple line and tissue 79 is placed within the jaw members 32 and 34 of the end effector 50. The instrument 15 is carefully positioned and fired such that a second cut line crosses the initial cut line and contains the tumor within a "V" shaped wedge (not shown) of tissue that is resected. As with lung volume reduction, the V shaped wedge is resected with the instrument 15 through the use of the clamping system, energy delivery system and the firing system such as mentioned in detail above.

While preferred embodiments of the present invention have been shown and described herein, it will be obvious to those skilled in the art that such embodiments are provided by way of example only. Numerous variations, changes, and substitutions will now occur to those skilled in the art without departing from the invention. Accordingly, it is intended that the invention be limited only by the spirit and scope of the appended claims.

What is claimed is:

1. A method for resecting a portion of lung, said method comprising the steps of:

a) clamping said portion of lung within an end effector of an electrosurgical instrument, said end effector having an upper jaw member and a lower jaw member being sufficiently stiff in order to provide pressure to said clamped portion of lung, said upper jaw member and said lower jaw member being spaced apart by said clamped portion of said lung when said end effector is clamped onto said portion of lung;

b) applying bipolar RF energy to said clamped portion of said lung to create a cauterized zone within said clamped portion of said lung;

c) stapling said cauterized zone with at least one staple;

d) cutting said cauterized zone adjacent to said at least one staple; and e) removing said portion of said lung.

2. The method of claim 1, wherein said cauterized zone is stapled with at least one row of staples.

3. A method for resecting a portion of lung, said method comprising the steps of:

a) clamping said portion of lung within an end effector of an electrosurgical instrument, said end effector having an upper jaw member and a lower jaw member being sufficiently stiff in order to provide pressure to said clamped portion of lung, said upper jaw member and said lower jaw member being spaced apart by said clamped portion of said lung when said end effector is clamped onto said portion of lung;

b) applying bipolar RF energy to said clamped portion of said lung to create a cauterized zone in said clamped portion of said lung;

c) stapling said cauterized zone with at least one staple;

d) stapling said clamped portion of lung adjacent to said cauterized zone with at least another staple;

e) cutting said portion of lung within said cauterized zone adjacent to said at least one staple; and f) removing said portion of said lung.

4. The method of claim 3, wherein said cauterized zone is stapled with at least one row of staples.

5. The method of claim 4, wherein said clamped portion of lung is stapled with at least another row of staples.

6. A method for resecting a portion of lung, said method comprising the steps of:

a) clamping said portion of lung with an end effector of an electrosurgical instrument, said end effector having an upper jaw member and a lower jaw member being sufficiently stiff in order to provide pressure to said clamped portion of lung, said upper jaw member and said lower jaw member being spaced apart by said clamped portion of said lung when said end effector is clamped onto said portion of lung;

b) applying bipolar RF energy to said clamped portion of said lung to create a cauterized zone in said clamped portion of said lung;

c) stapling said clamped portion of lung outside of said cauterized zone with at least one staple;

d) cutting said portion of lung within said cauterized zone; and e) removing said portion of said lung.

7. The method of claim 6, wherein said clamped portion of lung is stapled with at least one row of staples.

8. A method for resecting a portion of lung, said method comprising the steps of:

a) clamping said portion of lung within an end effector of an electrosurgical instrument, said end effector having an upper jaw member and a lower jaw member being sufficiently stiff in order to provide pressure to said clamped portion of lung, said upper jaw member and said lower jaw member being spaced apart by said clamped portion of said lung when said end effector is clamped onto said portion of lung;

b) stapling said clamped portion of lung with at least one staple;

c) applying bipolar RF energy to said clamped portion of said lung to create a cauterized zone adjacent to said at least one staple;

d) cutting said portion of lung within said cauterized zone; and f) removing said portion of said lung.

9. The method of claim 8, wherein said clamped portion of lung is stapled with at least one row of staples.

10. A method for resecting a portion of lung, said method comprising the steps of:

a) clamping said portion of lung with an end effector of an electrosurgical instrument, said end effector having an upper jaw member and a lower jaw member being sufficiently stiff in order to provide pressure to said clamped portion of lung, said upper jaw member and said lower jaw member being spaced apart by said clamped portion of said lung when said end effector is clamped onto said portion of lung;

b) applying bipolar RF energy to said clamped portion of said lung to create a cauterized zone in said clamped portion of said lung;

c) stapling said cauterized zone with at least one staple;

d) removing said end effector from said portion of lung;

e) cutting said cauterized zone adjacent to said at least one staple with a separate cutting instrument; and f) removing said portion of said lung.

11. The method of claim 9, wherein said cauterized zone is stapled with at least one row of staples.

12. The method of claim 10, wherein said cutting instrument is a pair of surgical scissors.

* * * * *